(12) United States Patent
Felder

(10) Patent No.: US 8,202,227 B2
(45) Date of Patent: Jun. 19, 2012

(54) PRESSURE SENSING ADAPTER FOR GASTRIC BAND SYSTEM INJECTOR

(75) Inventor: Kevin D. Felder, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 325 days.

(21) Appl. No.: 12/637,053

(22) Filed: Dec. 14, 2009

(65) Prior Publication Data

US 2011/0144530 A1    Jun. 16, 2011

(51) Int. Cl.
*A61B 5/00* (2006.01)
*A61F 2/00* (2006.01)
*A61F 2/02* (2006.01)

(52) U.S. Cl. ............... 600/561; 600/29; 600/30; 600/31

(58) Field of Classification Search ............. 600/29, 600/30, 31, 561; 73/1.72, 46, 862.72; 251/220, 251/304
See application file for complete search history.

(56) References Cited

U.S. PATENT DOCUMENTS

| | | | |
|---|---|---|---|
| 5,318,533 | A | 6/1994 | Adams et al. |
| 6,461,292 | B1 | 10/2002 | Forsell |
| 6,470,892 | B1 | 10/2002 | Forsell |
| 6,855,115 | B2 | 2/2005 | Fonseca et al. |
| 7,416,528 | B2 | 8/2008 | Crawford et al. |
| 7,442,165 | B2 | 10/2008 | Forsell |
| 7,621,863 | B2 | 11/2009 | Forsell |
| 2003/0225371 | A1 | 12/2003 | Hadzic et al. |
| 2005/0283118 | A1 | 12/2005 | Uth et al. |
| 2006/0211912 | A1 | 9/2006 | Dlugos et al. |
| 2006/0211914 | A1 | 9/2006 | Hassler, Jr. et al. |
| 2008/0250340 | A1 | 10/2008 | Dlugos, Jr. et al. |

FOREIGN PATENT DOCUMENTS

| | | |
|---|---|---|
| EP | 1 949 875 | 7/2008 |
| WO | WO 2009/023247 | 2/2009 |

OTHER PUBLICATIONS

International Search Report dated Apr. 14, 2011 for Application No. PCT/US10/059118.

*Primary Examiner* — Max Hindenburg
*Assistant Examiner* — Charles Becker
(74) *Attorney, Agent, or Firm* — Frost Brown Todd LLC (57) ABSTRACT

The body of a pressure sensing component includes a pressure sensor, a first opening, and a first pair of electrical contacts. A cap of the pressure sensing component comprises a second opening, a wiper seal, and a second pair of electrical contacts. The cap is rotatable relative to the body. When the cap is in a first rotational position, the first and second openings are in fluid communication with each other; and the first pair of contacts are not coupled with the second pair of contacts. When the cap is in a second rotational position, the seal isolates the first opening from the second opening; and the first pair of contacts are coupled with the second pair of contacts. The pressure sensing component may be coupled with a syringe and needle to externally adjust and monitor the pressure of fluid in an implanted gastric band system.

3 Claims, 6 Drawing Sheets

PRESSURE SENSING ADAPTER FOR GASTRIC BAND SYSTEM INJECTOR

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein.

In some settings, it may be desirable to obtain data indicative of the pressure of fluid in a gastric band. Various examples of methods and devices for obtaining pressure data are disclosed in U.S. Pub. No. 2006/0211912, entitled "External Pressure-Based Gastric Band Adjustment System and Method" published Sep. 21, 2006, the disclosure of which is incorporated by reference herein. Such pressure data may be used to determine whether the amount of fluid in the gastric band needs to be adjusted; and/or for other purposes.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIGS. 1-4 illustrate an exemplary gastric band system (10). As shown, gastric band system (10) comprises an injection port (12), a gastric band (20), and a catheter (18). Injection port (12) of the present example comprises a housing (14) and a needle penetrable septum (16). Housing (14) defines a fluid reservoir (not shown), such that a needle may pierce septum (16) to reach the reservoir and add or withdraw fluid (e.g., saline, etc.) as described in greater detail below. Housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, the disclosure of which is incorporated by reference herein. Alternatively, injection port (12) may have any other suitable configuration and/or operability.

Figure 1:
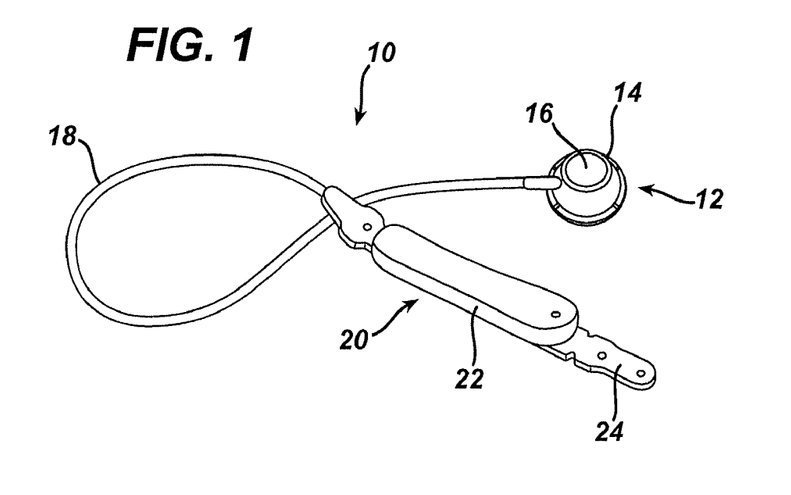
FIG. 1 depicts a perspective view of an implantable portion of an exemplary gastric band system.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
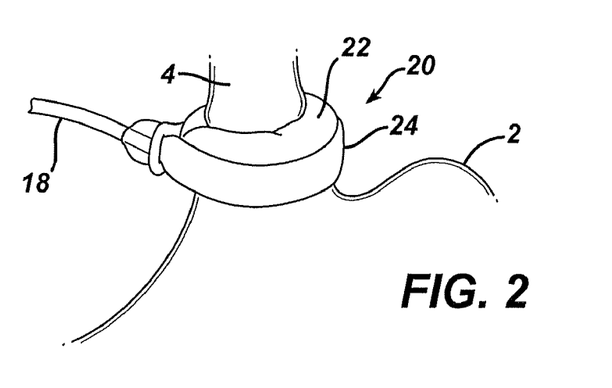
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
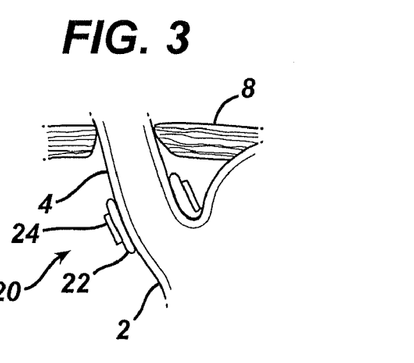
FIG. 3 depicts a cross-sectional view of the gastric band of FIG. 1, showing the band positioned around the gastro-esophageal junction of a patient in a deflated configuration.
Figure 4:
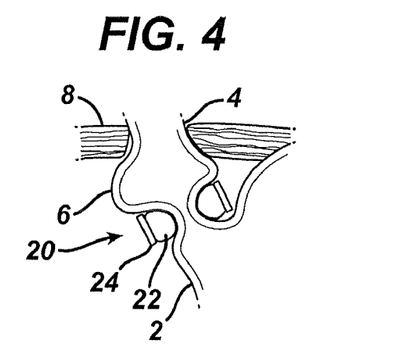
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

Figure 5:
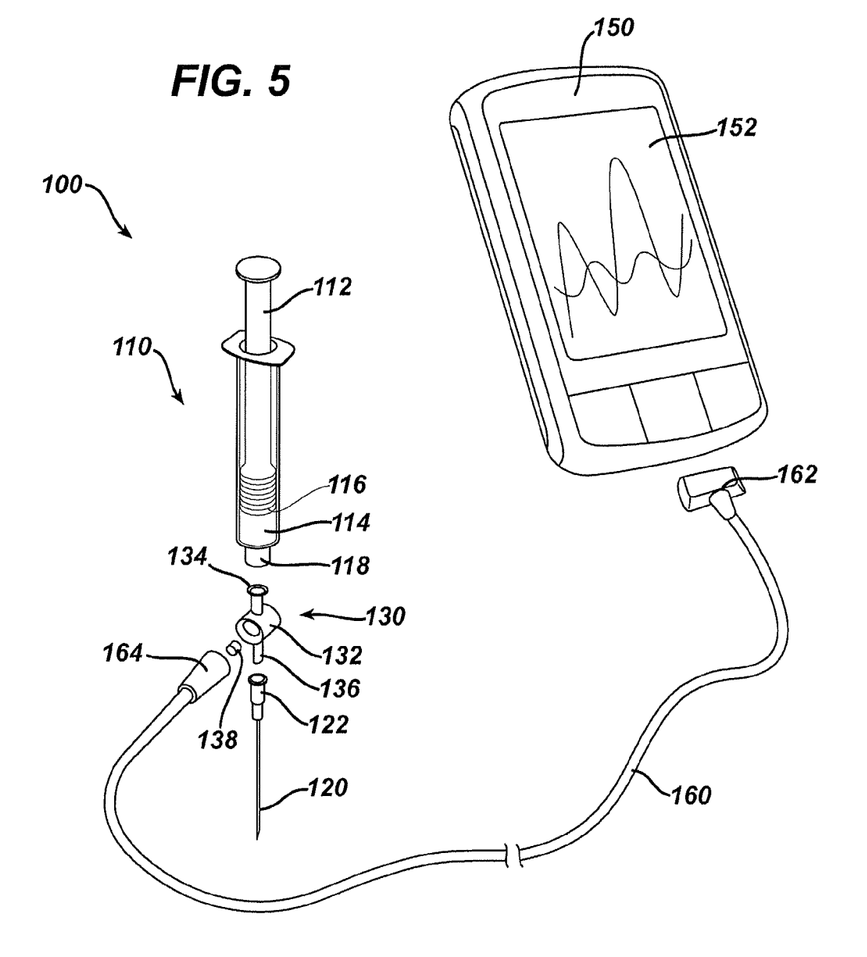
FIG. 5 depicts a perspective exploded view of an exemplary pressure sensing syringe system usable with the gastric band system of FIG. 1.

FIG. 5 shows an exemplary needle system (100) that may be used with gastric band system (10). In this example, needle system (100) comprises a syringe (110) and a display device (150) in communication via a cable (160). Syringe (110) comprises a plunger (112), a barrel (114), a pressure sensing component (130), and a needle (120). Plunger (112) includes a piston (116) that sealingly engages barrel (114). Barrel (114) includes a conventional luer lock portion (118) that is in fluid communication with the interior of barrel (114). Needle (120) comprises a conventional non-coring Huber needle, and includes a conventional luer lock portion (122). Of course, any of these components, among others, may be varied in any suitable fashion.

Pressure sensing component (130) of the present example comprises a body portion (132), an upper luer lock portion (134), a lower luer lock portion (136), and a pressure sensor (138). Upper luer lock portion (134) is configured to couple with luer lock portion (118) of syringe (110). Lower luer lock portion (136) is configured to couple with luer lock portion (122) of needle (120). It should therefore be understood that pressure sensing component (130) of the present example may be retrofitted to a variety of types of syringes and needles, etc. Body portion (132) provides communication of fluid between syringe (110) and needle (120). In addition, pressure sensor (138) is in fluid communication with the interior of body portion (132), such that pressure sensor (138) is operable to sense the pressure of fluid in syringe (110) and needle (120) as will be described in greater detail below. In some versions, pressure sensor (138) comprises a pressure sensor provided by CardioMEMS, Inc. of Atlanta, Ga., though any other suitable type of pressure sensor may be obtained from any other suitable source. By way of example only, pressure sensor (138) may be constructed in accordance with the teachings of U.S. Pat. No. 6,855,115, entitled "Implantable Wireless Sensor for Pressure Measurement within the Heart," issued Feb. 15, 2005, the disclosure of which is incorporated by reference herein. As another merely illustrative example, pressure sensor (138) may be constructed in accordance with the teachings of U.S. Pub. No. 2006/0211914, entitled "System and Method for Determining Implanted Device Positioning and Obtaining Pressure Data," published Sep. 21, 2006, the disclosure of which is incorporated by reference herein. Still other suitable forms that pressure sensor (138) may take will be apparent to those of ordinary skill in the art in view of the teachings herein.

Cable (160) of the present example has a boot portion (164), which is configured to selectively attach to pressure sensing component (130). Boot portion (164) includes a feature (not shown) that is operable to electrically engage with pressure sensor (138) and thereby communicate pressure readings obtained by pressure sensor (138) along cable (160). Such a feature may comprise one or more terminals (not shown) or any other suitable type(s) of feature(s) as will be apparent to those of ordinary skill in the art. In the present example, boot portion (164) is removably coupled with pressure sensing component (130), though it should be understood that such a coupling may be substantially permanent or integral, etc. The other end of cable (160) includes a connector (162) that couples with display device (150). Cable (160) is thereby operable to communicate data obtained by pressure sensor (138) to display device (150). Display device (150) is operable to process such data and render feedback to the user via display (152).

In some versions, display device (150) comprises a dedicated device constructed for the purpose of processing pressure data and providing graphical and/or textual output to the user via display (152). In some other versions, display device (150) comprises a conventional portable electronic device (e.g., a BlackBerry, an iPhone, a laptop computer, etc.) with software that is operable to process pressure data and provide graphical and/or textual output to the user. In still other versions, display device (150) comprises a desktop PC or other type of computer with software that is operable to process pressure data and provide graphical and/or textual output to the user. Still various other forms that display device (150) may take will be apparent to those of ordinary skill in the art in view of the teachings herein. It should also be understood that cable (160) may comprise a conventional USB cable or some other type of cable. Furthermore, cable (160) may be omitted in some versions, such as versions where pressure sensing component (130) is operable to communicate to display device (150) wirelessly. Examples of such wireless communication are disclosed in U.S. Pub. No. 2006/0211914, entitled "System and Method for Determining Implanted Device Positioning and Obtaining Pressure Data," published Sep. 21, 2006, the disclosure of which is incorporated by reference herein; while other examples of wireless communication will be apparent to those of ordinary skill in the art in view of the teachings herein.

In one merely exemplary use, where gastric band system (10) has been implanted in a patient, needle (120) is inserted into a patient to reach septum (16) of injection port (12). Upon such insertion, needle (120) is in fluid communication with gastric band system (10), such that the pressure of the fluid in gastric band system (10) and needle system (100) will be substantially equalized. It will therefore be appreciated that fluid pressure sensed by pressure sensor (138) may be indicative of the pressure of fluid within gastric band system (10). In some settings, such pressure information may be useful during a process of using needle system (100) to adjust fluid pressure of gastric band system (10) by adding or withdrawing fluid to or from gastric band system (10). In particular, the configuration of syringe (110) and pressure sensing component (130) may permit substantially simultaneous adjustment and reading of fluid pressure.

For instance, a user may first insert needle (120) into the patient to reach septum (16) of injection port (12). Upon pressure equalization, the user may then read the initial pressure via display device (150). It will be understood that pressure equalization may be determined by a pressure reading remaining substantially constant. The user may then add or withdraw fluid to or from gastric band system (10) using syringe; by pushing plunger (112) further into barrel (114) or withdrawing plunger (112) further from barrel (114), respectively. The user may monitor display device (150) during such adding/withdrawing of fluid to monitor the fluid pressure in substantially real time. To the extent that there is a delay between the user's manipulation of syringe (110) and the time the pressure substantially equalizes among syringe (110) and gastric band system (10), the user may simply wait until the pressure reading indicated through display device (150) becomes substantially constant. Still other suitable ways in which needle system (100) may be used in conjunction with a gastric band system (10) will be apparent to those of ordinary skill in the art in view of the teachings herein.

FIGS. 6-11 show an exemplary alternative pressure sensing component (200), which may be used in needle system (100) as a substitute for pressure sensing component (130) described above. In this example, pressure sensing component (200) comprises a sensor member (220) and a cap member (250). Each of these components will be described in greater detail below. As will be apparent from the following teachings, pressure sensing component (200) of this example is operable to selectively switch between (a) simultaneously providing an electrical coupling and sealing off a fluid coupling; and (b) simultaneously providing a fluid coupling and preventing the electrical coupling.

As shown in FIGS. 6, 9, and 10-11, sensor member (220) of the present example comprises a luer lock portion (222) and a cap engagement portion (224). As shown in FIGS. 10A-10B, the interior of sensor member (220) is hollow, permitting fluid to be communicated through sensor member (220) as will be described in greater detail below. A diaphragm (226) is positioned within the interior of sensor member (220) and is configured to flex in response to the pressure of fluid within the interior of sensor member (220). A strain gauge (228) is positioned on the opposite side of diaphragm (226). Strain gauge (228) is configured to detect flexing and/or stretching strain of diaphragm (226), such that strain gauge (228) can sense the pressure of fluid within the interior of sensor member (220) as a function of flexing of diaphragm (226). Diaphragm (226) and strain gauge (228) thus together provide a pressure sensor that is similar to a diaphragm-based sensor as described in U.S. Pub. No. 2006/0211914, entitled "System and Method for Determining Implanted Device Positioning and Obtaining Pressure Data," published Sep. 21, 2006, the disclosure of which is incorporated by reference herein. Of course, any other suitable type of pressure sensor may be used. By way of example only, sensor member (220) may be easily modified to incorporate any of the pressure sensing components, features, and/or configurations disclosed in U.S. Pub. No. 2006/0211914.

Figure 6:
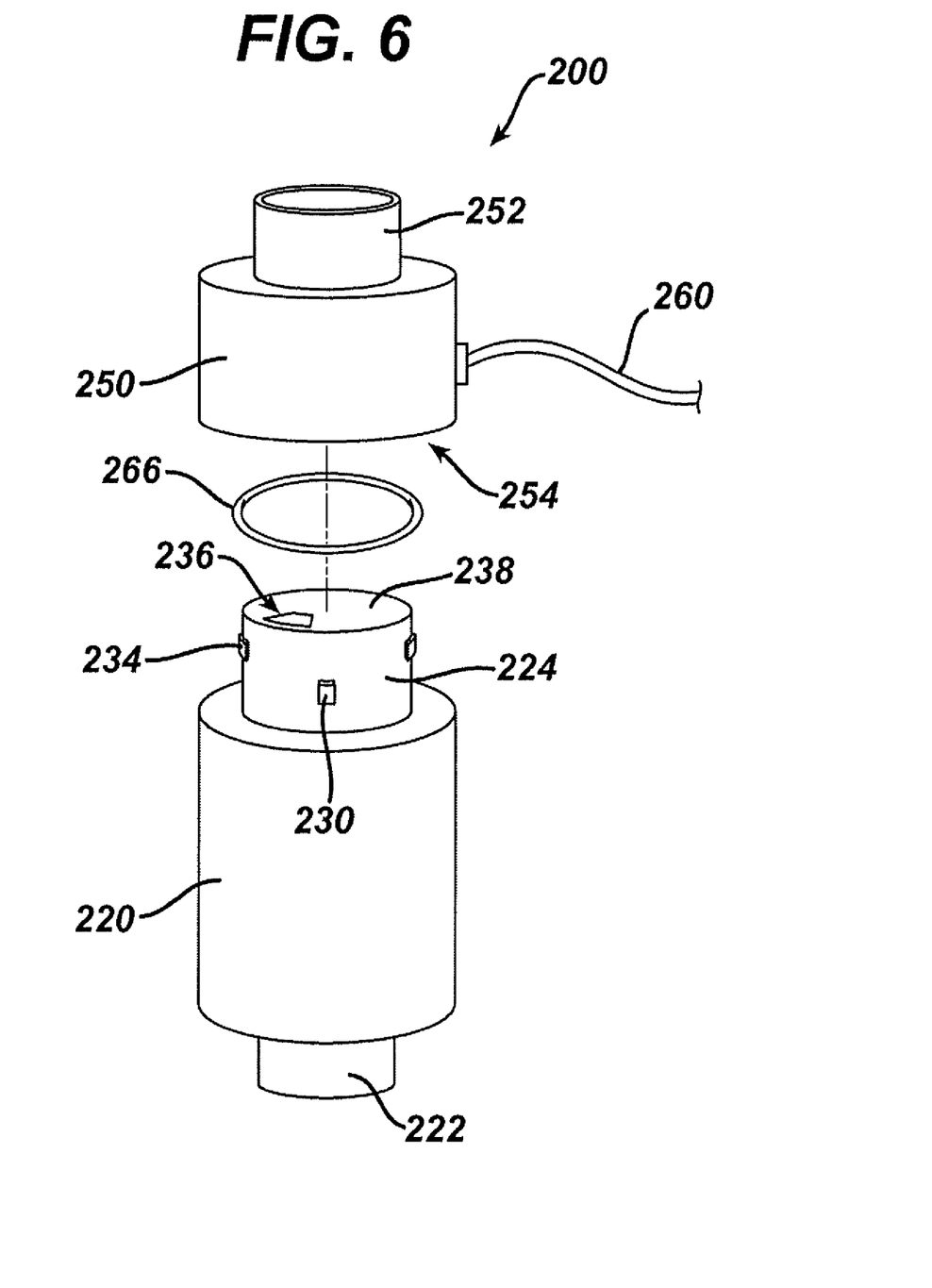
FIG. 6 depicts a perspective exploded view of an exemplary alternative pressure sensing component usable with the gastric band system of FIG. 1.
Figure 9:
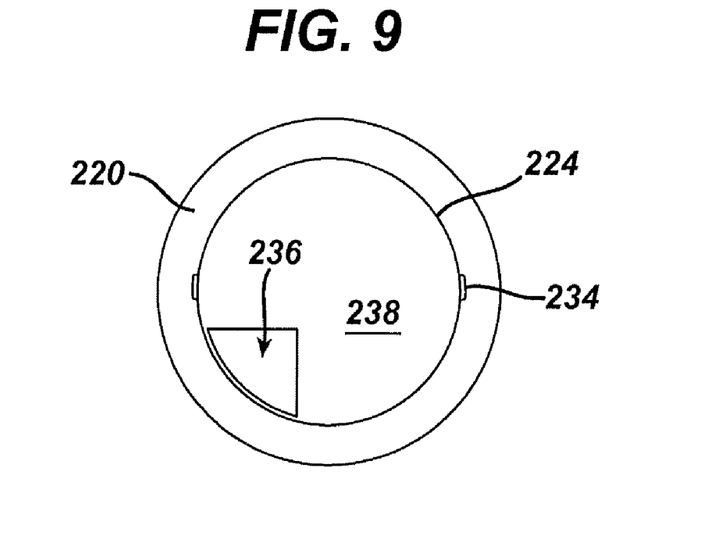
FIG. 9 depicts a top plan view of the sensor member of the pressure sensing component of FIG. 6.

In the present example, strain gauge (228) is in communication with electrical contacts (230). Contacts (230) are exteriorly exposed at cap engagement portion (224) of sensor member (220), at angular positions approximately 180° apart. While two opposing contacts (230) are provided in the present example, it should be understood that contacts (230) may alternatively be provided in any other suitable number and/or at any other suitable positioning. Strain gauge (228) is coupled with contacts (230) via wires (232). The configuration and mounting of diaphragm (226) hermetically seals strain gauge (228) and wires from fluid that is within the hollow interior of sensor member (220), such that strain gauge (228) and wires (232) remain substantially dry during use of pressure sensing component (200), even as pressurized fluid resides within the hollow interior of sensor member (220).

Cap engagement portion (224) also includes mounting protrusions (234) extending outwardly from its exterior sidewall. While there are two mounting protrusions (234) in diametrically opposed positions in the present example, it should be understood that mounting protrusions (234) may be provided in any other suitable number and/or position. The top of cap engagement portion (224) is defined by a horizontal wall (238), which is substantially perpendicular to the longitudinal axis of sensor member (220). An opening (236) is provided in horizontal wall (238). In particular, opening (236) of the present example has a wedge shape. When considering the top surface area vacated by opening (236) and the top surface area of horizontal wall (238) together as defining a circular surface area, the size of opening (236) is less than the size of a quadrant of such a circular surface area. Thus, a straight line extending across the center of horizontal wall (238) (e.g., a diameter line) may be angularly swept through an angular range of at least 90° without passing over opening (236). Put another way, a radius of horizontal wall (238) may be angularly swept through an angular range of at least 270° without passing over opening (236). Of course, this shape and positioning of opening (236) is merely exemplary. Opening (236) may have any other suitable size, shape, position, and/or relationship with horizontal wall (238). Similarly, horizontal wall (262) may have any other suitable size, shape, position, and/or relationship with opening (236). Various other suitable ways in which these features may be configured will be apparent to those of ordinary skill in the art in view of the teachings herein.

Opening (236) is in fluid communication with the hollow interior of sensor member (220). Luer lock portion (222) is also in fluid communication with the hollow interior of sensor member (220); and is configured to engage with luer lock portion (122) of needle (120). Accordingly, it should be understood that fluid may be communicated through opening (236), through the hollow interior of sensor member (220), and through luer lock portions (222, 122) to be communicated through needle (120).

Figure 7:
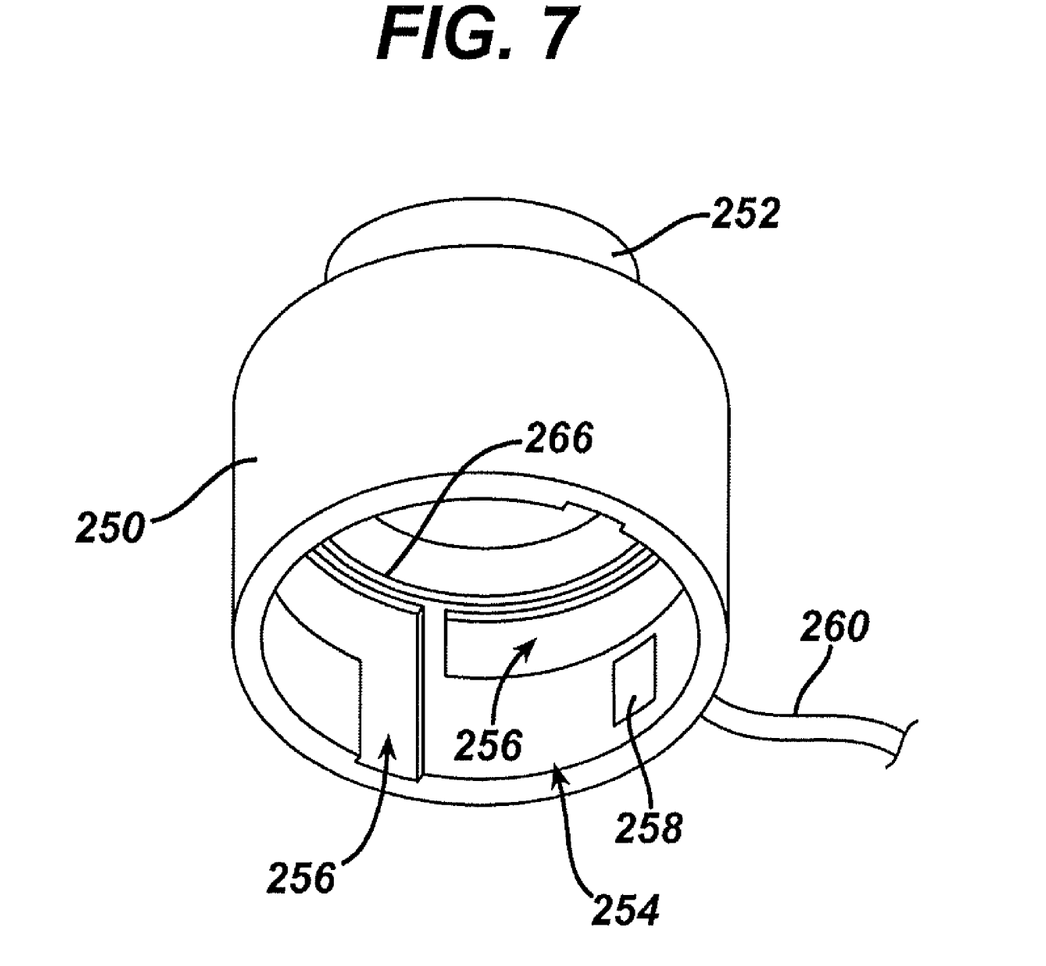
FIG. 7 depicts a bottom perspective view of the cap member of the pressure sensing component of FIG. 6.

As shown in FIGS. 6-8 and 10-11, cap member (250) of the present example comprises a luer lock portion (252) and a sensor engagement portion (254). Cap member (250) is configured to couple with syringe (110) at luer lock portion (252), such that luer lock portion (252) of cap member (250) mates with luer lock portion (118) of syringe (110). Sensor engagement portion (254) is configured to couple with sensor member (220). In particular, and as shown in FIG. 7, sensor engagement portion (254) comprises mounting recesses (256), which are configured to receive mounting protrusions (234) of sensor member (220). Mounting recesses (256) each include a longitudinally extending portion that receives a corresponding mounting protrusion (234) as cap member (250) is pushed longitudinally onto cap engagement portion (224) of sensor member (220). Mounting recesses (256) each also include a circumferentially extending portion that permits cap member (250) to be rotated relative to sensor member (220) once mounting protrusions (234) have been received in mounting recesses (256). Mounting recesses (256) of sensor engagement portion (254) and mounting protrusions (234) of sensor member (220) thus together provide a bayonet mount between cap member (250) and sensor member (220) in the present example, though it should be understood that any other suitable type of mount or fitting may be used. In the present example, each mounting recess (256) extends through an angular range of just less than 180°, permitting cap member (250) to be rotated just short of 180° when cap member (250) is coupled with sensor member (220). Alternatively, any other suitable angular range of motion may be provided. It should also be understood that a variety of other types of couplings may be provided between cap member (250) and sensor member (220), including but not limited screw-in fitting, press-in fitting, snap-in fitting, etc. Other suitable ways in which cap member (250) and sensor member (220) may be coupled together will be apparent to those of ordinary skill in the art in view of the teachings herein.

As is also shown in FIG. 7, sensor engagement portion (254) also includes interiorly exposed electrical contacts (258). Contacts (258) of sensor engagement portion (254) are configured and positioned to selectively engage contacts (230) of cap engagement portion (224) as will be described in greater detail below. Contacts (258) are further in communication with cable (261). As with cable (160) described above, cable (261) may be coupled with a display device (150) or a variety of other types of devices. Of course, cable (261) may instead be substituted or supplemented with a variety of other types of communication devices, including wireless communication devices (e.g., infrared transmitter, RF transmitter, etc.). Various suitable alternative communication devices are disclosed in U.S. Pub. No. 2006/0211914, entitled "System and Method for Determining Implanted Device Positioning and Obtaining Pressure Data," published Sep. 21, 2006, the disclosure of which is incorporated by reference herein. Other suitable types of alternative communication devices will be apparent to those of ordinary skill in the art in view of the teachings herein.

Figure 8:
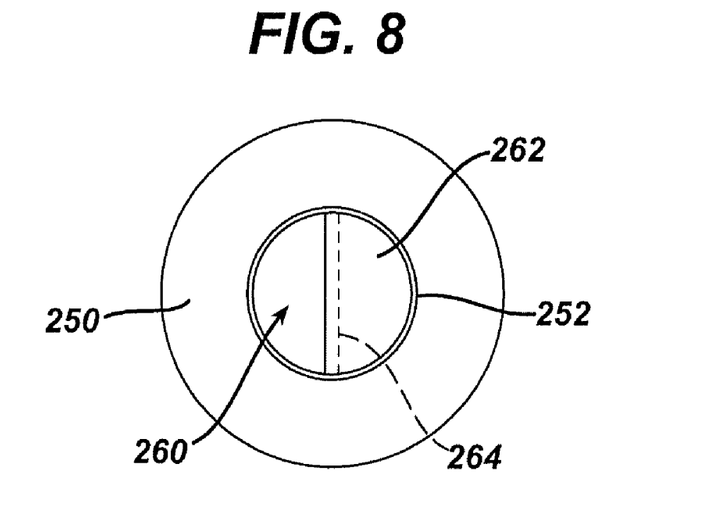
FIG. 8 depicts a top plan view of the cap member of the pressure sensing component of FIG. 6.
Figure 10A:
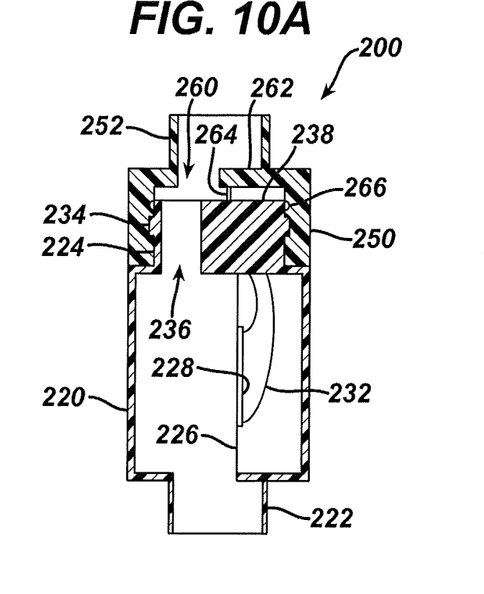
FIG. 10A depicts a cross-sectional view of the pressure sensing component of FIG. 6 in a first configuration.
Figure 10B:
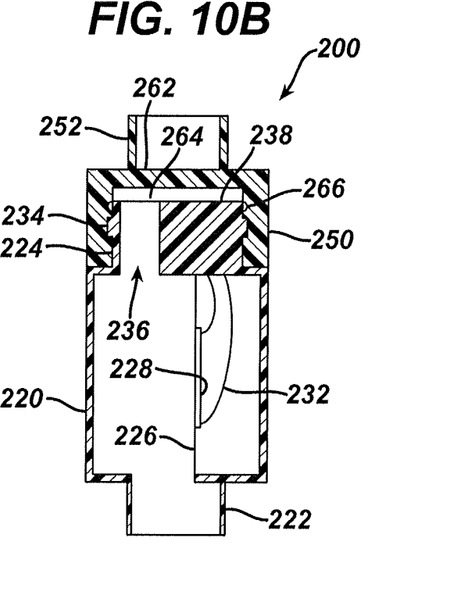
FIG. 10B depicts a cross-sectional view of the pressure sensing component of FIG. 6 in a second configuration.
Figure 11A:
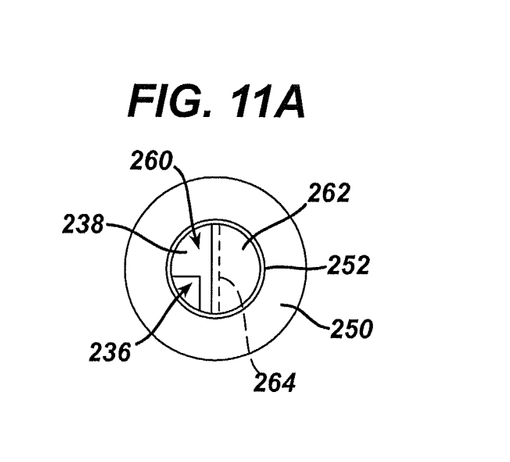
FIG. 11A depicts a top plan view of the pressure sensing component of FIG. 6 in the first configuration of FIG. 10A.
Figure 11B:
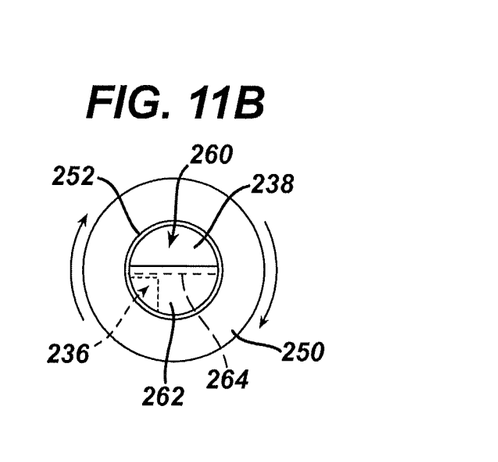
FIG. 11B depicts a top plan view of the pressure sensing component of FIG. 6 in the second configuration of FIG. 10B.

As shown in FIGS. 8 and 10-11, sensor engagement portion (254) of the present example further includes an opening (260), a horizontal wall (262) adjacent to opening (260), and a wiper seal (264). Horizontal wall (262) terminates just past a central diameter line of sensor engagement portion (254). Accordingly, the size of opening (260) is less than the top surface area of horizontal wall (262) in the present example. It should be understood, however, that opening (260) may have any suitable size, shape, position, and/or relationship with horizontal wall (262). Similarly, horizontal wall (262) may have any other suitable size, shape, position, and/or relationship with opening (260). Various other suitable ways in which these features may be configured will be apparent to those of ordinary skill in the art in view of the teachings herein. In the present example, wiper seal (264) extends downwardly from the underside of horizontal wall (262), and extends fully across the underside of horizontal wall (262). Wiper seal (264) is approximately centered along a diameter line of sensor engagement portion (264). Wiper seal (264) is also configured to engage horizontal wall (238) of cap engagement portion (224) of sensor member (220). In particular, wiper seal (264) is configured to resiliently bear against, and thereby provide a fluid seal against, horizontal wall (238). Such sealing provides selective fluid coupling or sealing between openings (236, 260) as a function of the rotational position of cap member (250) relative to sensor member (220), as will be described in greater detail below.

Opening (260) of sensor engagement portion (254) is configured to selectively communicate with opening (236) of cap engagement portion (224). In addition, wiper seal (264) is configured to substantially seal opening (260) relative to opening (236). As noted above, such sealing by wiper seal (264) is a function of the rotational position of cap member (250) relative to sensor member (220). In particular, when cap member (250) is in a first rotational position relative to sensor member (220), openings (236, 260) are substantially aligned as shown in FIGS. 10A and 11A. As is also shown in FIGS. 10A and 11A, wiper seal (264) does not substantially impede fluid communication between openings (236, 260) when cap member (250) is in the first rotational position. With openings (236, 260) substantially aligned, fluid may be communicated through opening (260) to opening (236) (or vice-versa). Of course, openings (236, 260) may be considered "substantially aligned" even if only part of opening (236) is aligned with only part of opening (260). Furthermore, some variations of pressure sensing component (200) may provide substantially unimpeded fluid communication between openings (236, 260) even when openings (236, 260) are completely non-aligned.

When cap member (250) is in a second rotational position relative to sensor member (220), openings are substantially non-aligned as shown in FIGS. 10B and 11B. In addition, wiper seal (264) substantially seals opening (260) relative to opening (236) when cap member (250) is in the second rotational position. Thus, fluid may not be communicated through opening (260) to opening (236) (or vice-versa) when cap member (250) is in the second rotational position relative to sensor member (220). Mounting recesses (256) and mounting protrusions (234) are configured to permit cap member (250) to be rotated back and forth between these first and second rotational positions, while still providing a substantially secure mechanical connection between sensor member (220) and cap member (250). An o-ring (266) may also be used to prevent leaking at the interface of sensor member (220) and cap member (250) when cap member (250) is at the first rotational position. Such an o-ring (266) may be positioned within an interior annular recess in cap member (250). Of course, o-ring (266) may be modified, substituted, supplemented, or omitted as desired. Similarly, it should be understood that wiper seal (264) is merely one example; and that wiper seal (264) may be modified, substituted, supplemented, or omitted as desired.

As noted above, contacts (258) of sensor engagement portion (254) are configured and positioned to selectively engage contacts (230) of cap engagement portion (224). In particular, contacts (258) engage contacts (230) when cap member (250) is at the second rotational position shown in FIGS. 10B and 11B. By contrast, contacts (258) are not engaged with contacts (230) when cap member (250) is at the first rotational position shown in FIGS. 10A and 11A. O-ring (266) may also substantially isolate contacts (230, 258) from fluid that is communicated through pressure sensor component (200), even when cap member (250) is in the first rotational position. In view of the foregoing, it should be understood that contacts (230, 258) are engaged when fluid communication between sensor member (220) and cap member (250) is prevented by wiper seal (264); while contacts (230, 258) are disengaged when fluid communication between sensor member (220) and cap member (250) is permitted. Either or both sets of contacts (230, 258) may be resiliently biased to promote engagement of contacts (230) with contacts (258) when cap member (250) is at the second rotational position.

As noted above, contacts (232) are in communication with strain gauge (228) via wires (232), while strain gauge (228)

senses deformation or strain of diaphragm (226) in response to fluid pressure. As also noted above, contacts (250) are in communication with cable (261), which may be coupled with display device (150). The communication of pressure data to display device (150) is thus a function of the rotational position of cap member (250) relative to sensor member (220) in the present example. As noted above, the opening or closing of the fluid path between openings (236, 260) is also a function of the rotational position of cap member (250) relative to sensor member (220) in the present example It should therefore be understood that pressure sensing component (200) will simultaneously provide a coupling between openings (236, 260) and a disconnect between contacts (232, 258) when cap member (250) is at the first rotational position shown in FIGS. 10A and 11A; and that pressure sensing component (200) will simultaneously provide a seal between openings (236, 260) and a coupling of contacts (232, 250) when cap member (250) is at the second rotational position shown in FIGS. 10B and 11B. In other words, pressure sensing component (200) provides sensing of fluid pressure within gastric band system (10) and communication of fluid pressure data to display device (150) when the fluid path from syringe (110) to needle (120) has been sealed off by wiper seal (264). Furthermore, pressure sensing component (200) may be adjusted to provide a fluid path from syringe (110) to needle (120) (e.g., by rotating cap member (250) relative to sensor member (220)), though pressure sensing component (200) does not provide fluid pressure to display device (150) when such fluid path is open in this particular example.

In a merely exemplary use of pressure sensing component (200), the user (e.g., physician, clinician, etc.) first fills barrel (114) of syringe (110) with saline or some other fluid. Then, the user aligns mounting protrusions (234) with the longitudinally extending portions of mounting recesses (256) and pushes cap member (250) onto sensor member (220). The user then rotates cap member (250) slightly relative to sensor member (220) to position mounting protrusions (234) in the circumferentially extending portions of mounting recesses (256). Next, the user couples luer lock portion (118) of syringe (110) with luer lock portion (252) of cap member (250); and couples luer lock portion (122) of needle (120) with luer lock portion (222) of sensor member (220). The user then couples cable (261) with display device (150). At this stage, pressure sensing component (200) is assembled and fully coupled with needle (120) and syringe (110). The user may "prime" pressure sensing component (200) and needle (120) by advancing plunger (112) until fluid exits needle (120). Cap member (250) may be rotated to the first rotational position as shown in FIGS. 10A and 11A during such priming.

The user then inserts needle (120) into septum (16) of an injection port (12) that is implanted in a patient. The user may then rotate cap member (250) relative to sensor member (220) (e.g., clockwise, viewed from top down) until cap member (250) reaches the second rotational position shown in FIGS. 10B and 11B. The user then waits momentarily for the pressure of fluid in gastric band system (10) to substantially equalize with the pressure of fluid in sensor member (220). Openings (236, 260) are sealed off from each other by wiper seal (264) at this stage, such that gastric band system (10) is fluidly isolated from syringe (110). Since contacts (230, 258) are engaged at this stage, pressure data sensed using diaphragm (226) and strain gauge (228) is communicated to display device (150). The user reads display device (150) to determine if fluid needs to be added to or withdrawn from gastric band system (10). The user may also have the patient drink water or some other substantially equivalent media at this stage to observe the effects of drinking on the pressure of fluid in gastric band system (10). The user then rotates cap member (250) relative to sensor member (220) (e.g., counterclockwise, viewed from top down) until cap member (250) reaches the first rotational position shown in FIGS. 10A and 11A. At this stage, contacts (230, 258) have been disengaged such that display device (150) no longer shows pressure data. However, the fluid path between openings (236, 260) is now open at this stage. The user may then adjust the pressure of fluid within gastric band system (10) using syringe (110), by moving plunger (112) upwardly or downwardly in barrel (114).

After the user has added or withdrawn fluid to or from gastric band system (10), the user may again rotate cap member (250) relative to sensor member (220) (e.g., clockwise, viewed from top down) until cap member (250) again reaches the second rotational position shown in FIGS. 10B and 11B. At this stage, opening (260) is sealed off from opening (260) by wiper seal (264), such that the pressure of fluid in gastric band system (10) will not urge plunger (112) upwardly or downwardly in barrel (114). In other words, wiper seal (264) fluidly isolates barrel (114) from gastric band system (10). Such prevention of movement of plunger (112) may help provide a more accurate and consistent reading of fluid pressure (e.g., otherwise, positive fluid pressure may drive plunger (112) upwardly, which may result in a drop in sensed fluid pressure). In addition, contacts (230, 258) are re-engaged at this stage, allowing the user to view updated pressure data on display device (150). The user may alternate between the first and second rotational positions of cap member (250) to make fluid pressure adjustments and take fluid pressure readings, respectively, until the desired level of fluid pressure in gastric band system (10) is obtained.

In some settings, the user may need to remove syringe (110) from pressure sensing component (200), such as to add more fluid to syringe (110), during the process of adjusting gastric band system (10). It should be understood that syringe (110) may be removed from pressure sensing component (200) without causing fluid leakage through pressure sensing component (200). In particular, the user may simply rotate cap member (250) to the second rotational position shown in FIGS. 10B and 11B, then decouple luer lock portion (118) of syringe (110) from luer lock portion (252) of cap member (250). After adding more fluid to syringe (110), the user may re-couple luer lock portion (118) of syringe (110) with luer lock portion (252) of cap member (250), then rotate cap member (250) back to the first rotational position shown in FIGS. 10A and 11A to make further adjustments to gastric band system (10).

It should be understood that the foregoing features, components, configurations, and uses of pressure sensing component (200) are merely exemplary; and that the same may be modified in numerous ways. For instance, luer lock portions (222, 252) are merely illustrative, and it should be understood that pressure sensing component (200) may be coupled with syringe (110) and/or needle (120) in any other suitable fashion. In addition, cap member (250) and/or sensor member (220) may include complementary detent features or other types of features that correspond with the first and second rotational positions shown in FIGS. 10-11. For instance, such detent features or other types of features may provide some degree of resistance to rotation when cap member (250) is at the first and/or second rotational position. Furthermore, such detent features or other types of features may provide audible and/or tactile feedback to the user to indicate that cap member (250) has reached the first and/or second rotational position. In addition or in the alternative, markings or other indicia may be provided on the exterior of cap member (220) and sensor member (220) to provide visual feedback indicating whether cap member (250) is in the first or second rotational position.

It should also be understood that the rotational engagement of cap member (250) with sensor member (220) is just one merely illustrative example. Cap member (250) may couple with sensor member (220) in any other suitable fashion. Furthermore, the sealing of opening (236) relative to opening (260) may be a function of some other type of movement of cap member (250), in addition to or in lieu of being a function of rotation of cap member (250) relative to sensor member (220). For instance, pressure sensing component (200) may be configured such that cap member (250) must be moved longitudinally relative to sensor member (220) to obtain a seal between openings (236, 260). Alternatively, pressure sensing component (200) may be configured such that cap member (250) must be moved longitudinally relative to sensor member (220) and then rotated relative to sensor member (220) to obtain a seal between openings (236, 260). Likewise, the coupling of contacts (232, 258) may be a function of some other type of movement of cap member (250), in addition to or in lieu of being a function of rotation of cap member (250) relative to sensor member (220). For instance, pressure sensing component (200) may be configured such that cap member (250) must be moved longitudinally relative to sensor member (220) to obtain coupling of contacts (232, 258). Alternatively, pressure sensing component (200) may be configured such that cap member (250) must be moved longitudinally relative to sensor member (220) and then rotated relative to sensor member (220) to obtain a coupling of contacts (232, 258).

As yet another merely illustrative variation, contacts (232, 258) may be configured such that they are substantially continuously coupled, regardless of whether openings (236, 260) are sealed off from each other or are in fluid communication with each other. For instance, contacts (232, 258) may comprise slip rings and/or leaf springs, etc. Furthermore, pressure sensing component (200) may be configured such that cap member (250) and sensor member (220) are substantially inseparable rather than being provided as separate parts. That is, pressure sensing component (200) may be provided as a single integral device that may be coupled with syringe (110) and needle (120). Such an integral pressure sensing component (200) may nevertheless include at least one feature that is rotatable or otherwise movable relative to another feature to provide selective fluid communication between syringe (110) and needle (120) and/or to provide selective communication between strain gauge (228) and display device (150). Still other suitable variations of pressure sensing component (200) will be apparent to those of ordinary skill in the art in view of the teachings herein.

Pressure data obtained using pressure sensing component (200) may be processed presented on display device (150) in a variety of ways. In addition, the user may react to such pressure data in a variety of ways. Various suitable ways in which pressure data may be processed, presented, and reacted to are disclosed in U.S. Pub. No. 2008/0250340, entitled "GUI for an Implantable Restriction Device and Data Logger," published Oct. 9, 2008, the disclosure of which is incorporated by reference herein. Other ways in which pressure data may be processed, presented, and reacted to are disclosed in U.S. Pub. No. 2006/0211914, entitled "System and Method for Determining Implanted Device Positioning and Obtaining Pressure Data," published Sep. 21, 2006, the disclosure of which is incorporated by reference herein. Still other suitable ways in which pressure data may be processed, presented, and reacted to will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

It will also be readily apparent to those skilled in the art that examples described herein may have applicability to other types of devices (i.e., not just implantable bands per se). For instance, a syringe (110) and needle (120) fitted with a pressure sensing component (200) may be used to adjust the pressure of fluid within a gastric balloon or other volume occupying device; the pressure of fluid within an infusion port; etc. Various other types of devices and systems with which the examples described herein may be used will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. The apparatus, comprising:
   (a) a body having a hollow interior portion, wherein the body comprises:
      (i) a first opening in communication with the hollow interior portion,
      (ii) a pressure sensing device in communication with the hollow interior portion, and
      (iii) a first port in communication with the hollow interior portion, wherein the first port is configured to couple with a selected one of a syringe or a needle;
   (b) a cap coupled with the body, wherein the cap comprises:
      (i) a second opening,
      (ii) a seal, wherein the seal is configured to selectively seal the first opening relative to the second opening when the cap is at a first position relative to the body, wherein the seal is further configured to selectively permit fluid communication between the first opening and the second opening when the cap is at a second position relative to the body, and
      (iii) a second port in communication with the second opening, wherein the second port is configured to couple with a selected one of a syringe or a needle; and
   (c) a communication device coupled with the cap, wherein the communication device is configured to selectively couple with the pressure sensing device when the cap is at the first position, wherein the communication device is further configured to transmit pressure data to an external device when the communication device is coupled with the pressure sensing device.

2. The apparatus of claim 1, wherein the communication device comprises a cable.

3. The apparatus of claim 1, wherein the body comprises a first electrical contact in communication with the pressure sensing device, wherein the cap comprises a second electrical contact in communication with the communication device, wherein the first and second electrical contacts are configured such that the first and second electrical contacts are coupled together when the cap is at the first position, wherein the first and second electrical contacts are configured such that the first and second electrical contacts are not coupled together when the cap is at the second position.

* * * * *